(12) United States Patent
Baseeth

(10) Patent No.: US 10,882,019 B2
(45) Date of Patent: Jan. 5, 2021

(54) LECITHIN MICROEMULSIONS AND USES THEREOF

(71) Applicant: Archer Daniels Midland Company, Decatur, IL (US)

(72) Inventor: Shireen S. Baseeth, Decatur, IL (US)

(73) Assignee: ARCHER DANIELS MIDLAND COMPANY, Decatur, IL (US)

( * ) Notice: Subject to any disclaimer, the term of this patent is extended or adjusted under 35 U.S.C. 154(b) by 0 days.

(21) Appl. No.: 15/750,303

(22) PCT Filed: Aug. 5, 2016

(86) PCT No.: PCT/US2016/045718
§ 371 (c)(1),
(2) Date: Feb. 5, 2018

(87) PCT Pub. No.: WO2017/024205
PCT Pub. Date: Feb. 9, 2017

(65) Prior Publication Data
US 2018/0214839 A1    Aug. 2, 2018

Related U.S. Application Data

(60) Provisional application No. 62/201,378, filed on Aug. 5, 2015.

(51) Int. Cl.
| | | |
|---|---|---|
| *A61K 47/14* | (2017.01) | |
| *A61K 47/36* | (2006.01) | |
| *B01J 13/10* | (2006.01) | |
| *C11D 1/66* | (2006.01) | |
| *C11D 17/00* | (2006.01) | |
| *A61K 31/685* | (2006.01) | |
| *C11D 3/20* | (2006.01) | |
| *C11D 3/43* | (2006.01) | |
| *A61K 8/06* | (2006.01) | |
| *A61K 8/37* | (2006.01) | |
| *A61K 8/55* | (2006.01) | |
| *A61K 8/73* | (2006.01) | |
| *A61K 9/107* | (2006.01) | |
| *A61K 47/24* | (2006.01) | |
| *A61K 47/26* | (2006.01) | |
| *A61Q 19/00* | (2006.01) | |
| *C08J 3/215* | (2006.01) | |
| *C08L 5/00* | (2006.01) | |
| *C08L 71/02* | (2006.01) | |
| *C11D 1/94* | (2006.01) | |
| *C11D 1/36* | (2006.01) | |

(52) U.S. Cl.
CPC ............... *B01J 13/10* (2013.01); *A61K 8/068* (2013.01); *A61K 8/37* (2013.01); *A61K 8/553* (2013.01); *A61K 8/73* (2013.01); *A61K 9/1075* (2013.01); *A61K 31/685* (2013.01); *A61K 47/14* (2013.01); *A61K 47/24* (2013.01); *A61K 47/26* (2013.01); *A61K 47/36* (2013.01); *A61Q 19/00* (2013.01); *C08J 3/215* (2013.01); *C08L 5/00* (2013.01); *C08L 71/02* (2013.01); *C11D 1/662* (2013.01); *C11D 1/667* (2013.01); *C11D 1/94* (2013.01); *C11D 3/2093* (2013.01); *C11D 3/43* (2013.01); *C11D 17/0021* (2013.01); *A61K 2800/10* (2013.01); *A61K 2800/412* (2013.01); *C08J 2305/00* (2013.01); *C08J 2371/02* (2013.01); *C08J 2405/00* (2013.01); *C08J 2471/02* (2013.01); *C11D 1/36* (2013.01)

(58) Field of Classification Search
CPC ...... A61K 31/685; A61K 47/14; A61K 47/24; A61K 47/26; A61K 47/36; A61K 8/068; A61K 8/37; A61K 8/553; A61K 8/73; A61K 9/1075; A61K 2800/10; A61K 2800/412; A61Q 19/00; B01J 13/10; C08J 3/215; C08J 2305/00; C08J 2371/02; C08J 2405/00; C08J 2471/02; C08L 5/00; C08L 71/02; C11D 1/662; C11D 1/667; C11D 1/94; C11D 17/0021; C11D 3/2093; C11D 3/43; C11D 1/36

See application file for complete search history.

(56) References Cited

U.S. PATENT DOCUMENTS

2010/0034880 A1*  2/2010  Sintov .................. A61K 9/0014
                                                    424/484

FOREIGN PATENT DOCUMENTS

WO    WO-2013134267 A1 *  9/2013  ............. A01N 25/04

\* cited by examiner

*Primary Examiner* — Irina S Zemel
(74) *Attorney, Agent, or Firm* — Andrew F. Niles

(57) ABSTRACT

The present disclosure is directed to compositions including a microemulsion comprising lecithin, a polysorbate, an alkyl polyglycoside, and optionally a solvent. Uses of the microemulsions are also disclosed.

10 Claims, 2 Drawing Sheets

LECITHIN MICROEMULSIONS AND USES THEREOF

CROSS-REFERENCE TO RELATED APPLICATIONS

This application is a national stage entry of International Application No. PCT/US2016/45718, filed Aug. 5, 2016, which itself claims priority to U.S. Provisional Patent Application No. 62/201,378, filed Aug. 5, 2015, each of the contents of the entirety of which is incorporated by this reference.

TECHNICAL FIELD

The present disclosure relates generally to microemulsions. More particularly, the present disclosure relates to the production and use of lecithin containing microemulsions.

BACKGROUND

A microemulsion is a self-assembled transparent or nearly transparent system that is an isotropic and thermodynamically stable mixture of two immiscible liquids stabilized by a surfactant or mixture of surfactants. Small chain molecules such as co-surfactants may be added to the microemulsions. The microemulsions are formed by self-assembly and no high shear homogenization is required in forming these microemulsions. Based on the microemulsion's composition of oil, water, and a surfactant, the microemulsions can be categorized as oil/water, water/oil, or single phase bicontinuous microemulsions.

Based on the stability of microemulsions, they have been exploited in a wide array of applications such as food, pharmaceuticals, fuel, industrial, cosmetic and personal care, in delivery systems, and even in biocatalysis. Microemulsions are also often used in degreasers, cleaners, and agricultural adjuvants. When low oil content compounds (e.g., terpenes, methyl esters, etc . . . ) are used in an oil in water microemulsion, such microemulsions can be diluted in water and function as a good cleaner. As microemulsions are shelf stable and are able to solubilize in water, microemulsions are used to disperse water insoluble actives and find utility as delivery systems in the agrochemical space.

Although there are wide number of microemulsions that are commercially used in a variety of applications, there is always a need for raw materials used in microemulsions that are environmentally benign. Attempts to provide environmentally friendly microemulsions are disclosed in U.S. Pat. No. 8,138,120 which discloses the use of alkylpolyglycoside surfactants in ag adjuvants and in U.S. Pat. No. 8,455,426 which discloses which discloses the use of alkylpolyglycoside surfactants in cleaners.

While some biobased microemulsions have been developed, needs exist for additional biobased microemulsions that have more functionality and are more economical to produce.

SUMMARY

In each of its various embodiments, the present invention fulfills these needs and discloses lecithin containing microemulsions that are biobased and have utility in all industrial microemulsion systems.

In one embodiment, a microemulsion comprises lecithin, a polysorbate, and an alkyl polyglycoside. Uses of the microemulsion are also disclosed.

In a further embodiment, a microemulsion concentrate comprises lecithin, a poly sorbate, an alkyl polyglycoside, and a solvent. Uses of the microemulsion concentrate to disperse or solubilize compounds (such as nonpolar compounds) in water are further disclosed. In a further embodiment, a gelling agent such as a gum may be mixed with the water.

It should be understood that this disclosure is not limited to the embodiments disclosed in this Summary, and it is intended to cover modifications that are within the spirit and scope of the invention, as defined by the appended claims.

DETAILED DESCRIPTION

Figure 1:
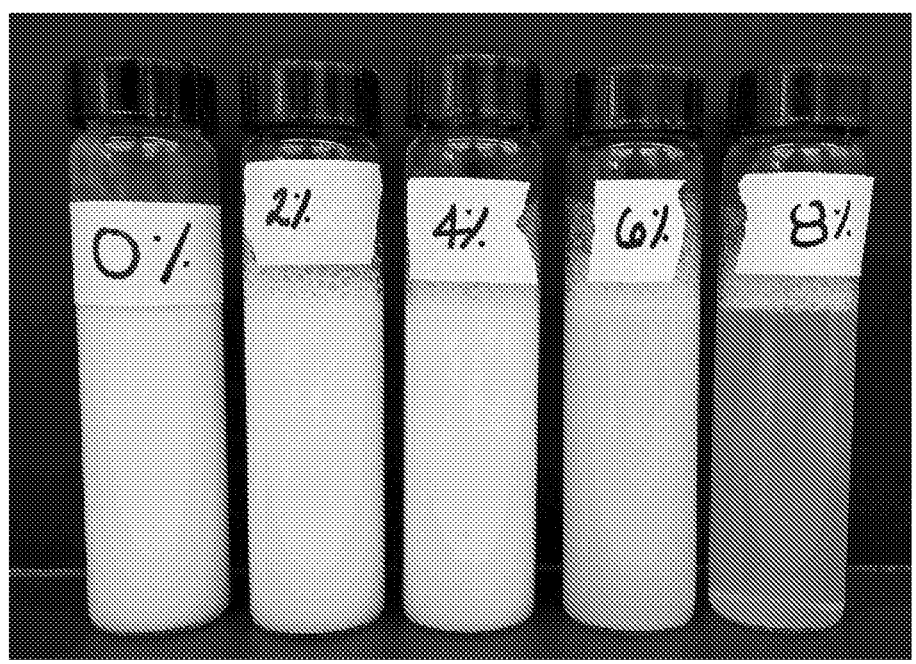
FIG. 1 shows pictures of various embodiments of the microemulsion of the present invention.

One benefit of the microemulsions of the present invention is that they are thermodynamically stable one phase systems that are isotropic and form instant stable emulsions once added to water. Such characteristic of the microemulsions of the present invention is that they may be used as a surfactant concentrate that can solubilize different types of oils or nonpolar compounds and provide tremendous opportunities towards applications based on the specific oil or nonpolar compound needs. Such products offer advantages as far as cost savings and transportation are concerned. This offers a great advantage in shipping the microemulsion in this form where the water is required only at the time of application, not at the time of microemulsion formation.

In the present application, including the claims, other than in the operating examples or where otherwise indicated, all numbers expressing quantities or characteristics are to be understood as being modified in all instances by the term "about". Unless indicated to the contrary, any numerical parameters set forth in the following description may vary depending on the desired properties in the compositions and methods according to the present disclosure. At the very least, and not as an attempt to limit the application of the doctrine of equivalents to the scope of the claims, each numerical parameter described in the present description should at least be construed in light of the number of reported significant digits and by applying ordinary rounding techniques.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, the disclosure set forth herein supersedes any conflicting material incorporated herein by reference.

In each of the various embodiments, the present invention is directed towards lecithin containing microemulsions and uses thereof.

Lecithin is an amphiphile of considerable potential interest from a fundamental and an applied point (Interfacial tensions for lecithin microemulsions including the effect of surfactant and polymer addition; K. Shinoda, Y. Shibata and B. Lindman; Langmuir, 1993, 9 (5), pp 1254-1257). The present invention utilizes the ability of lecithin to form different types of microemulsions.

Lecithin is a byproduct obtained from vegetable oil refining. Lecithin is a polar lipid chiefly including phospholipids. A typical crude soybean lecithin contains about 50% of mixed phospholipids (i.e., (phosphatidyl choline (PC), phosphatidyl ethanolamine (PE), phosphatidylserine (PS), and phosphatidyl inositol (PI)), about 34% triglycerides, glycolipids, carbohydrates, and other minor ingredients. Lecithin can be obtained in fluid and deoiled form. The deoiled lecithin has high phospholipids, is substantially free of any oils, and can be used in many microemulsion formulations alone or optionally in combination with other surfactants. In one embodiment, alkyl polyglycosides showed very good synergy in making clear microemulsions in combination with lecithin.

The polar lipid aspect of lecithin has some interesting properties and therefore is used in many agricultural adjuvant formulations. However, lecithin is rarely used in industrial applications. Lecithin has the advantage of being a renewable emulsifier and can be used to improve the carbon foot print of formulations to which its added. In an embodiment of the present invention, the microemulsion formulations have >98% biobased content.

Lecithin is a lipid substance found in animal and plant tissues such as, for example, egg yolk, soybean, sunflower, and canola or rapeseed. The amphiphilic property of lecithin makes it an effective processing aid, emulsifier, dispersant and/or surfactant. Lecithin is also a natural ingredient than can form nanodispersions in aqueous mediums and carry high loads of actives. But, in such aqueous mediums, lecithin may have limited tolerance to pH and electrolytes.

Lecithin may be used in applications where modification of the boundary layer between substances is desirable. In the presence of an immiscible liquid phase, lecithin can reduce the interfacial surface tension and function as an emulsifier. When used with two or more solid phases, lecithin can function as a lubricant and/or release agent.

In one embodiment, a lecithin based microemulsion of the present invention has utility in a solubilizing or dispersing oils, such as at a neutral pH. Oils that may be solubilized or dispersed include, but are not limited to, linseed oil, pine oil, soy methyl ester, coconut oil, soybean oil, high oleic oils, mineral oil, limonene, any oil of wide fatty acid profile, and combinations of any thereof.

In one embodiment, a microemulsion comprises lecithin and a co-surfactant. The microemulsion may further comprise a salt of an acidifier, an ester of an acidifier, or combinations thereof. In another embodiment, the microemulsion may have a neutral pH.

Also, yet another embodiment of this invention describes a process for producing a microemulsion by mixing lecithin with a polysorbate and an alkyl polyglycoside. A solvent such as an ester of an organic acid may also be added to the microemulsion.

In yet other embodiments, microemulsion concentrates of the present invention may be used in concrete applications, in oil field applications, or in cleaning and/or degreasing formulations. One aspect of this embodiment describes the use of bio-based and bio-renewal components for preparing such microemulsion concentrates.

In one embodiment, the microemulsion concentrates of the present invention when used as agents to solubilize oils are added to water, an oil, and mixed.

Microemulsions are clear, isotropic, thermodynamically stable liquid mixtures including oil, water, and a surfactant. The water phase may contain salt(s) and/or other ingredients. Microemulsions may be prepared from a large number of components. In contrast to ordinary emulsions, microemulsions form upon simple mixing of the components and do not require high shear conditions. In ternary systems, such as micro emulsions, where two immiscible phases (water and 'oil') are present next to the surfactant phase, the surfactant molecules form a monolayer at the interface between oil and water, with the hydrophobic tails of the surfactant molecules dissolved in the oil phase and the hydrophilic head groups in the aqueous phase. Comparable to the binary systems (water/surfactant or oil/surfactant), self-assembled structures of different morphologies can be obtained ranging from (inverted) spherical and cylindrical micelles to lamellar phases and bi-continuous microemulsions. A water-in-oil microemulsion is an optically transparent mixture including oil, water, and surfactant. Water droplets are in a continuous oil phase stabilized by surfactant.

Lecithins suitable for use in the disclosed compositions and methods include, but are not limited to, crude filtered lecithin, fluid lecithin, de-oiled lecithin, chemically and/or enzymatically modified lecithin, standardized lecithin, and blends of any thereof. Lecithins employed in the present disclosure generally tend to have a hydrophilic-lipophilic balance ("HLB") value ranging from 1.0 to 10.0 depending on the processing conditions and additives used to obtain and produce the lecithin product. For example, crude filtered lecithin has an HLB value of approximately 4.0 and favors the formation of water-in-oil emulsions. Standardized lecithin includes co-emulsifiers having HLB values ranging from 10.0 to 24.0, which results in lecithin compositions having HLB values of 7.0 to 12.0 and favoring oil-in-water emulsions. Any lecithin or combinations of lecithins are suitable for use in the disclosed compositions and methods regardless of the initial HLB value of the lecithin. Lecithins useful in the disclosed compositions and methods may comprise co-emulsifiers having a hydrophilic-lipophilic balance value ranging from 10.0 to 24.0, and in certain embodiments 10.0 to 18.0.

The emulsifier and/or surfactant properties of an amphiphilic substance such as lecithin, for example, may be predicted at least in part by the hydrophilic-lipophilic balance ("HLB") value of the substance. The HLB value may function as an index of the relative preference of an amphiphilic substance for oil or water—the higher the HLB value, the more hydrophilic the molecule; the lower the HLB value, the more hydrophobic the molecule. A description of HLB values is provided in U.S. Pat. No. 6,677,327, which is incorporated by reference herein in its entirety. HLB is also described in Griffin, "Classification of Surface-Active Agents by 'HLB,'" *J. Soc. Cosmetic Chemists* 1 (1949); Griffin, "Calculation of HLB Values of Non-Ionic Surfactants," *J. Soc. Cosmetic Chemists* 5 (1954); Davies, "A quantitative kinetic theory of emulsion type, I. Physical chemistry of the emulsifying agent," *Gas/Liquid and Liquid/Liquid Interfaces, Proceedings of the 2d International Congress on Surface Activity* (1957); and Schick, "Nonionic Surfactants: Physical Chemistry", Marcel Dekker, Inc., New York, N.Y., pp. 439-47 (1987), each of which is incorporated by reference herein in its entirety.

Substances of a bio-derived origin are derived from biological materials as opposed to being derived from petrochemical sources. Bio-derived substances may be differentiated from petroleum derived substances by their carbon isotope ratios using ASTM International Radioisotope Standard Method D 6866. As used herein, the term "bio-derived" refers to being derived from or synthesized by a renewable biological feedstock, such as, for example, an agricultural, forestry, plant, fungal, bacterial, or animal feedstock.

Various agencies have established certification requirements for determining bio-derived content. These methods require the measurement of variations in isotopic abundance between bio-derived products and petroleum derived products, for example, by liquid scintillation counting, accelerator mass spectrometry, or high precision isotope ratio mass spectrometry. Isotopic ratios of the isotopes of carbon, such as the $^{13}C/^{12}C$ carbon isotopic ratio or the $^{14}C/^{12}C$ carbon isotopic ratio, can be determined using isotope ratio mass spectrometry with a high degree of precision. Studies have shown that isotopic fractionation due to physiological processes, such as, for example, $CO_2$ transport within plants during photosynthesis, leads to specific isotopic ratios in natural or bio-derived compounds. Petroleum and petroleum derived products have a different $^{13}C/^{12}C$ carbon isotopic ratio due to different chemical processes and isotopic fractionation during the generation of petroleum. In addition, radioactive decay of the unstable $^{14}C$ carbon radioisotope leads to different isotope ratios in bio-derived products compared to petroleum products. Bio-derived content of a product may be verified by ASTM International Radioisotope Standard Method D 6866. ASTM International Radioisotope Standard Method D 6866 determines bio-derived content of a material based on the amount of bio-derived carbon in the material or product as a percent of the weight (mass) of the total organic carbon in the material or product. Bio-derived products will have a carbon isotope ratio characteristic of a biologically derived composition.

Bio-derived materials offer an attractive alternative for industrial manufacturers looking to reduce or replace their reliance on petrochemicals and petroleum derived products. The replacement of petrochemicals and petroleum derived products with products and/or feed stocks derived from biological sources (i.e., bio-based products) offer many advantages. For example, products and feed stocks from biological sources are typically a renewable resource. In most instances, bio-derived chemicals and products formed therefrom are less burdensome on the environment than petrochemicals and products formed from petrochemicals. As the supply of easily extracted petrochemicals continues to be depleted, the economics of petrochemical production will likely force the cost of the petrochemicals and petroleum derived products to be higher compared to bio-based products. In addition, companies may benefit from the marketing advantages associated with bio-derived products from renewable resources in the view of a public becoming more concerned with the supply of petrochemicals.

In various embodiments, the disclosed compositions may also comprise one or more co-surfactants. The one or more co-surfactants may comprise one or more anionic surfactants, one or more non-ionic surfactants, or combinations of one or more anionic surfactants and one or more non-ionic surfactants. In various embodiments, the co-surfactant or co-surfactant combinations may have a hydrophilic-lipophilic balance ranging from 10.0 to 24.0, and in some embodiments from 10.0 to 18.0.

Anionic surfactants suitable for use in the disclosed compositions and methods include, but are not limited to, sodium and potassium salts of straight-chain fatty acids, polyoxyethylenated fatty alcohol carboxylates, linear alkyl benzene sulfonates, alpha olefin sulfonates, sulfonated fatty acid methyl ester, arylalkanesulfonates, sulfosuccinate esters, alkyldiphenylether(di)sulfonates, alkylnaphthalenesulfonates, isoethionates, alkylether sulfates, sulfonated oils, fatty acid monoethanolamide sulfates, polyoxyethylene fatty acid monoethanolamide sulfates, aliphatic phosphate esters, nonylphenolphosphate esters, sarcosinates, fluorinated anionics, anionic surfactants derived from oleochemicals, and combinations of any thereof. In various embodiments, the surfactant comprises an anionic surfactant, such as, for example, a phosphate ester.

Non-ionic surfactants suitable for use in the disclosed compositions and methods include, but are not limited to, sorbitan monostearate, polyoxyethylene ester of rosin, polyoxyethylene dodecyl mono ether, polyoxyethylene-polyoxypropylene block copolymer, polyoxyethylene monolaurate, polyoxyethylene monohexadecyl ether, polyoxyethylene monooleate, polyoxyethylene mono(cis-9-octadecenyl) ether, polyoxyethylene monostearate, polyoxyethylene monooctadecyl ether, polyoxyethylene dioleate, polyoxyethylene distearate, polyoxyethylene sorbitan monolaurate polyoxyethylene sorbitan monooleate, polyoxyethylene sorbitan monopalmitate, polyoxyethylene sorbitan monostearate, polyoxyethylene sorbitan trioleate, polyoxyethylene sorbitan tristearate, polyglycerol ester of oleic acid, polyoxyethylene sorbitol hexastearate, polyoxyethylene monotetradecyl ether, polyoxyethylene sorbitol hexaoleate, fatty acids, tall-oil, sorbitol hexaesters, ethoxylated castor oil, ethoxylated soybean oil, rapeseed oil ethoxylate, ethoxylated fatty acids, ethoxylated fatty alcohols, ethoxylated polyoxyethylene sorbitol tetraoleate, glycerol and polyethylene glycol mixed esters, alcohols, polyglycerol esters, monoglycerides, sucrose esters, alkyl polyglycosides, polysorbates, fatty alkanolamides, polyglycol ethers, derivatives of any thereof, and combinations of any thereof. In various embodiments, the surfactant comprises a non-ionic surfactant, such as, for example, a fatty acid ethoxylate.

In another embodiment, the compositions of the present invention may be food grade and include a food grade surfactant such as, for example, a polysorbate. In an embodiment, the polysorbate may be an oily liquid derived from PEG-ylated sorbitan (a derivative of sorbitol) esterified with a fatty acid. Non-limiting examples of polysorbate include, but are not limited to, polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate), and polysorbate 80 (polyoxyethylene (20) sorbitan monooleate).

In a further embodiment, the composition of the present invention includes an alkyl polyglycoside which may be made by a fatty alcohol and a sugar. A non-limiting example of an alkyl polyglycoside that may be used includes, without limitation, alkyl polyglucosides.

The embodiments disclosed herein are also directed to methods or processes of preparing the disclosed compositions. In various embodiments, lecithin is mixed with a cosurfactant (such as a polysorbate and/or an alkyl polyglycoside) at ambient temperature and constantly stirred for a period of time. In another embodiment, a solvent (such as an ester of an organic acid) is added to the lecithin/co-surfactant blend at ambient temperature and mixed for a period of time, thus forming a microemulsion concentrate.

EXAMPLES

The following exemplary, non-limiting examples are provided to further describe the embodiments presented herein. Those having ordinary skill in the art will appreciate that variations of these Examples are possible within the scope of the invention.

Examples 1-5

Microemulsion formulations were made with soy methyl ester (B100, available from Archer-Daniels-Midland Company, Decatur, Ill.), Polysorbate 80 (T Maz 80 available from BASF), alkylpolyglycoside based on C8-C16 natural fatty alcohol (Glucopon 425 available from BASF), and de-oiled lecithin (Yelkinol AC available from Archer-Daniels-Midland Company, Decatur, Ill.). The formulations are shown in Table 1.

TABLE 1

Soy methyl ester (SME) based microemulsions.

| Ingredient | Example 1 | Example 2 | Example 3 | Example 4 | Example 5 |
|---|---|---|---|---|---|
| soy methyl ester | 35% | 35% | 35% | 35% | 35% |
| alkylpolyglycoside | 27% | 26% | 25% | 24% | 23% |
| polysorbate 80 | 27% | 26% | 25% | 24% | 23% |
| ethyl lactate | 11% | 11% | 11% | 11% | 11% |
| lecithin | 0% | 2% | 4% | 6% | 8% |

The microemulsions were made by mixing the ingredients using gentle mixing. The de-oiled lecithin came in powdered form and was dissolved in the soy methyl ester and ethyl lactate before being added to the surfactant package. The microemulsion concentrates of Examples 1-5 were all clear, transparent, and stable at temperatures of 10-40° C.

The microemulsion formulations Examples 1-5 were dispersed in water to produce a 10% active soy methyl ester solution. As can be seen in FIG. 1, the microemulsion formulations are shown from left to right ranging from the addition of 0% lecithin to 8% lecithin. As the concentration of the lecithin increases, the soy methyl ester dilutions result in microemulsions that maintain their structural integrity. The microemulsions in Examples 1-4 upon dilution form oil in water microemulsions. Microemulsions have the lowest interfacial tension. In a system containing the alkylpolyglycoside and the polysorbate, the presence of the lecithin contributes towards lowering the interfacial tension to a point that results in more water dilutable microemulsions. The synergistic interaction of the alkylpolyglycoside, the polysorbate, and the lecithin may find utility in a cleaning composition where clear products are preferred.

Example 6

Taking advantage of the water dilutable clear microemulsion produced in Example 5, the formulation of Table 2 was used to produce a clear microemulsion.

TABLE 2

| Ingredient | Percentage (%) |
|---|---|
| soy methyl ester | 39 |
| alkylpolyglycoside | 21 |
| polysorbate | 21 |
| ethyl lactate | 10 |
| lecithin | 9 |

The microemulsion was produced substantially as described with regards to Examples 1-5. The microemulsion produced according to Table 2 was diluted at a ratio of 40:60 with water, thus producing a clear, oil in water microemulsion.

Example 7

The microemulsion dilution of Example 6 was used to load iron (III) chloride and 10% green tea extract (GTE) to produce zerovalent iron particles. The formulations of Table 3 were used to produce an iron chloride microemulsion (µ Fe(III)) and a green tea extract microemulsion (µ green tea extract (GTE)).

TABLE 3

| Ingredient | µ Fe(III) | µ green tea extract (GTE) |
|---|---|---|
| Microemulsion of Example 6 | 40% | 40% |
| Fe(III) chloride solution (1.5M) | 60% | — |
| Green tea extract (10% solution) | — | 60% |

The microemulsion µ Fe(III) has 0.9M iron and 40% of this microemulsion was added to 60% of the microemulsion µ GTE to form a zero valent iron microemulsion µ Fe(0) with an effective concentration of 9.8% Fe(0). This Example shows how the microemulsions of the present invention may be used as nanoreactors by mixing two different microemulsions containing two different reactants (i.e., iron chloride and green tea extract) to form a third microemulsion containing a product (i.e., zero valent iron).

Example 8

The microemulsion of Example 6 was diluted to 40% in water per the formulation of Table 4.

TABLE 4

| | Microemulsion gel |
|---|---|
| Microemulsion of Example 6 | 40% |
| 1% (w/v) xanthan gum solution (Novaxan 80 available from Archer Daniels Midland Company, Decatur, Illinois | 60% |

Figure 2:
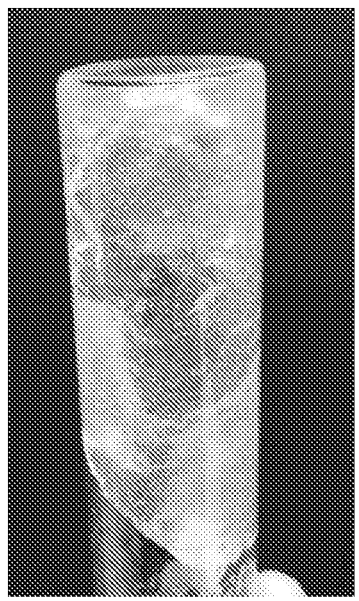
FIG. 2 shows a picture of one embodiment of a microemulsion of the present invention.

The microemulsion gel produced from this Example is shown in FIG. 2.

This disclosure has been described with reference to certain exemplary embodiments, compositions, and uses thereof. However, it will be recognized by those of ordinary skill in the art that various substitutions, modifications, or combinations of any of the exemplary embodiments may be made without departing from the spirit and scope of the disclosure. Thus, the disclosure is not limited by the description of the exemplary embodiments, but rather by the appended claims as originally filed.

What is claimed is:

1. A microemulsion concentrate having a pH of between 5 and 9 consisting of:
   1-15% by weight lecithin;
   15-35% by weight of a polysorbate;
   15-35% by weight of an alkyl polyglycoside;
   5-15% by weight of a solvent; and
   a non-polar compound.

2. The microemulsion of claim 1, wherein the solvent is an ester of an organic acid.

3. The microemulsion of claim 2, wherein the ester is an alkyl ester.

4. The microemulsion of claim 1, wherein the lecithin is selected from the group consisting of crude filtered lecithin, de-oiled lecithin, chemically modified lecithin, enzymatically modified lecithin, standardized lecithin, and combinations of any thereof.

5. The microemulsion of claim 1, wherein the non-polar compound is a methyl ester.

6. A method of dispersing a nonpolar compound comprising:
dissolving powdered, de-oiled lecithin in the non-polar compound and a solvent;
mixing the lecithin, the non-polar compound and the solvent with a polysorbate and an alkyl polyglycoside, thus forming a microemulsion concentrate;
wherein the microemulsion concentrate consists of 1-15% by weight of the powdered, de-oiled lecithin, 5-15% by weight of the solvent, 15-35% by weight of the polysorbate, and 15-35% by weight of the alkyl polyglycoside; and
dispersing the microemulsion concentrate in water.

7. The method according to claim 6, wherein the nonpolar compound is selected from the group consisting of oil, soy methyl ester, and limonene.

8. The method according to claim 6, further comprising mixing a gelling agent with the water.

9. The method according to claim 8, wherein the gelling agent is a gum.

10. The microemulsion of claim 1, wherein the microemulsion is at least 98% biobased.

\* \* \* \* \*